US006350880B1

(12) United States Patent
Katsura et al.

(10) Patent No.: US 6,350,880 B1
(45) Date of Patent: Feb. 26, 2002

(54) CRYSTALLINE OR CRYSTALLIZED ACID ADDITION SALT OF LOSARTAN AND PURIFICATION METHOD OF LOSARTAN

(75) Inventors: Tadashi Katsura; Hiroshi Shiratani; Nobushige Itaya, all of Osaka (JP)

(73) Assignee: Sumika Fine Chemicals Co., Ltd., Osaka (JP)

( * ) Notice: Subject to any disclaimer, the term of this patent is extended or adjusted under 35 U.S.C. 154(b) by 0 days.

(21) Appl. No.: 09/714,339

(22) Filed: Nov. 16, 2000

(30) Foreign Application Priority Data

Dec. 6, 1999 (JP) ............................................. 11-346829
Sep. 19, 2000 (JP) ............................................. 12-282853

(51) Int. Cl.[7] ........................................... C07D 257/04
(52) U.S. Cl. ........................ 548/252; 548/254; 548/250
(58) Field of Search ................................. 548/250, 252, 548/254

(56) References Cited

U.S. PATENT DOCUMENTS 5,128,355 A * 7/1992 Carini et al. ................. 514/381
5,464,854 A * 11/1995 dePadova ..................... 514/381

FOREIGN PATENT DOCUMENTS

| WO | 93/10106 | 5/1993 |
| WO | 95/17396 | 6/1995 |
| WO | WO 98/18787 | 5/1998 |
| WO | 99/67231 | 12/1999 |

* cited by examiner

Primary Examiner—Floyd D. Higel
Assistant Examiner—Andrea D'Souza Small
(74) Attorney, Agent, or Firm—Leydig, Voit & Mayer, Ltd.

(57) ABSTRACT

The present invention provides a crystalline or crystallized acid addition salt of Losartan useful for obtaining highly pure 2-n-butyl-4-chloro-1-[[2'-(1H-tetrazol-5-yl)[1,1'-biphenyl]-4-yl]methyl]-1H-imidazole-5-methanol (Losartan), and a purification method of Losartan that includes production of the crystalline or crystallized acid addition salt.

6 Claims, No Drawings

CRYSTALLINE OR CRYSTALLIZED ACID ADDITION SALT OF LOSARTAN AND PURIFICATION METHOD OF LOSARTAN

TECHNICAL FIELD OF THE INVENTION

The present invention relates to a novel crystalline or crystallized acid addition salt of Losartan, which has a superior antagonistic activity against angiotensin II, and to a purification method of Losartan, which comprises producing the crystalline or crystallized acid addition salt.

BACKGROUND OF THE INVENTION 2-n-Butyl-4-chloro-1-[[2'-(1H-tetrazol-5-yl)[1,1'-biphenyl]-4-yl]methyl]-1H-imidazole-5-methanol of the following formula (Ia)

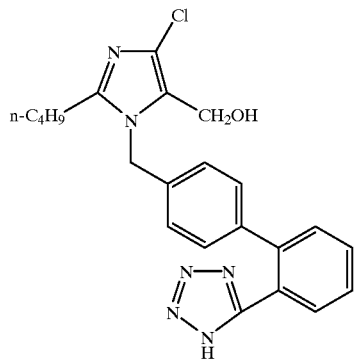

(Ia)

(hereinafter to be also referred to as Losartan) is a useful antihypertensive agent having a superior antagonistic activity against angiotensin II. Losartan is generally used in the form of a potassium salt. Inasmuch as purification of a potassium salt is not feasible, it is a typical practice to purify free Losartan to a high degree first and then convert it to a potassium salt.

However, purification of Losartan itself is also difficult and there are some purification methods proposed to achieve a higher purity of Losartan (WO93/10106, WO95/17396 etc.). These methods, nevertheless, are not entirely satisfactory and a feasible purification method to increase the purity of Losartan has been demanded.

SUMMARY OF THE INVENTION

It is therefore an object of the present invention to provide a crystalline or crystallized acid addition salt of Losartan, which is useful for producing highly pure Losartan. Another object of the present invention is to provide an easy purification method for obtaining highly pure Losartan.

According to the present invention, there is provided a crystalline or crystallized acid addition salt of 2-n-butyl-4-chloro-1-[[2'-(1H-tetrazol-5-yl)[1,1'-biphenyl]-4-yl]methyl]-1H-imidazole-5-methanol (Losartan) of the formula (I)

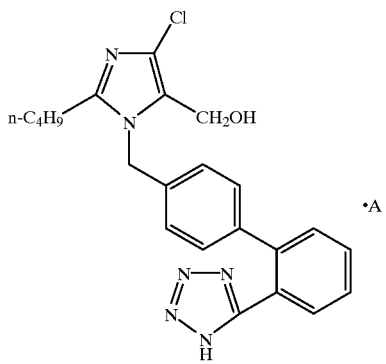

(I)

wherein A is an acid.

Preferably, A in the above-mentioned formula (I) is selected from the group consisting of hydrochloric acid, hydrobromic acid and p-toluenesulfonic acid, with more preference given to p-toluenesulfonic acid.

Preferably, when A in the above-mentioned formula (I) is p-toluenesulfonic acid, the above-mentioned crystalline or crystallized acid addition salt is in the form of a solvate, wherein the solvent that forms the solvate is preferably tetrahydrofuran.

The present invention also provides a purification method of Losartan, which comprises a step for obtaining a crystalline or crystallized acid addition salt of Losartan of the formula (I)

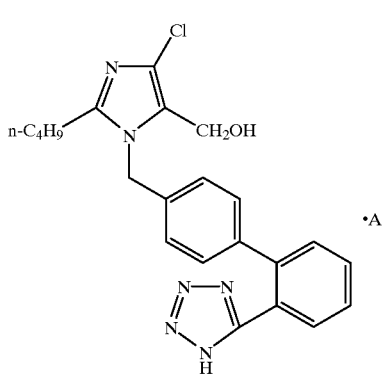

(I)

wherein A is an acid, formed from Losartan and the acid.

Preferably, the acid (A) is selected from the group consisting of hydrochloric acid, hydrobromic acid and p-toluenesulfonic acid, with preference given to p-toluenesulfonic acid.

Preferably, when the acid (A) is p-toluenesulfonic acid, the above-mentioned crystalline or crystallized acid addition salt is in the form of a solvate, wherein the solvent that forms the solvate is preferably tetrahydrofuran.

Preferably, the above-mentioned crystalline or crystallized acid addition salt is formed in an organic solvent.

Preferably, the above-mentioned crystalline or crystallized acid addition salt in the form of a solvate is formed in a solvent containing a solvent that can form the solvate.

Preferably, the above-mentioned tetrahydrofuran solvate is formed in a solvent containing tetrahydrofuran.

DETAILED DESCRIPTION OF THE INVENTION

The crystalline or crystallized acid addition salt of Losartan of the above-mentioned formula (I) of the present invention is an acid addition salt formed from Losartan of the above-mentioned formula (Ia), which is a known compound, and an acid at an imidazole moiety of Losartan. The salt has crystallinity (i.e., property to become crystals) or is in the form of crystals. The solvates (e.g., monosolvate, disolvate, 1/2 solvate, 1/3 solvate, 1/4 solvate, 2/3 solvate, 3/2 solvate and the like) of the crystalline or crystallized acid addition salt are also encompassed in the present invention. Examples of the solvent to form the solvate include water, organic solvents such as ethers [e.g., tetrahydrofuran (THF) and the like] and lower alcohols having 1 to 4 carbon atoms (e.g., methanol, ethanol, propanol, butanol and the like), and the like.

The acid represented by A in the above-mentioned crystalline or crystallized acid addition salt is free of any particular limitation as long as the acid can form a crystalline or crystallized acid addition salt at the imidazole moiety of Losartan. Examples of the acid include hydrochloric acid, hydrobromic acid, p-toluenesulfonic acid and the like. Of these, p-toluenesulfonic acid is preferable because the resulting crystalline or crystallized acid addition salt shows a high purity.

Since the above-mentioned crystalline or crystallized acid addition salt can be highly pure in the state of a solvate depending on the kind of acid, when the solvate is highly pure, it may be preferably in the form of a solvate in some cases.

Examples of preferable crystalline or crystallized acid addition salt mentioned above include hydrochloride, hydrobromide and p-toluenesulfonate, more preferably p-toluenesulfonate, particularly preferably p-toluenesulfonate THF solvate.

The Losartan in the above-mentioned crystalline or crystallized acid addition salt is a known compound, which can be produced according to a known method.

The above-mentioned-crystalline or crystallized acid addition salt can be produced from Losartan and the above-mentioned acid according to a method known as a general production method of acid addition salts. Preferably, Losartan is dissolved in an organic solvent capable of dissolving Losartan, such as monochlorobenzene (MCB), THF and the like, and an acid is added to the resulting solution.

Since the above-mentioned crystalline or crystallized acid addition salt can be purified to a high purity level, it is useful for obtaining highly pure Losartan. In other words, highly pure Losartan or a potassium salt etc. thereof can be obtained easily from the crystalline or crystallized acid addition salt.

The purification method of Losartan of the present invention is based on the finding that the crystalline or crystallized acid addition salt of Losartan, which is formed from Losartan and the above-mentioned acid, can be purified to a high level. The method comprises a step for obtaining a crystalline or crystallized acid addition salt of Losartan, which is formed from Losartan and the above-mentioned acid: a step for obtaining a crystalline or crystallized acid addition salt of Losartan by precipitation.

As used herein, by "obtaining a crystalline or crystallized acid addition salt of Losartan" is meant obtaining a crystalline or crystallized acid addition salt of Losartan as a real substance. Therefore, obtaining a crystalline or crystallized acid addition salt of Losartan dissolved in a solution state is not included in the context of "obtaining a crystalline or crystallized acid addition salt of Losartan".

Losartan used as a starting compound in the purification method of the present invention can be any that is produced according to an optional production method, with no limitation imposed on purity and the like. It may be a known salt at the tetrazole moiety of Losartan, such as a potassium salt and the like. Examples of the salt of Losartan include salt with alkali metal, such as sodium, potassium, lithium and the like; salt with alkaline earth metal, such as calcium, magnesium and the like; salt with organic base, such as triethylamine, diisopropylethylamine and the like; and the like. These salts may be used in combination of two or more kinds thereof. When these salts are used as starting materials in the purification method of the present invention, a step for producing free Losartan by a conventionally-known method may be added as necessary before a step for producing a crystalline or crystallized acid addition salt.

The above-mentioned Losartan is preferably purified by an optional purification step to increase purity of the obtained crystalline or crystallized acid addition salt of Losartan. Examples of such purification step include conventionally-known methods such as recrystallization, chromatography and the like. Preferably, an alkali is added to an organic solvent containing Losartan to make pH thereof not less than 12 to allow Losartan present in an aqueous layer, and an organic layer containing impurities is separated and removed. The alkali to be used for this method may be caustic alkali (e.g., sodium hydroxide, potassium hydroxide and the like), alkali carbonate (e.g., sodium carbonate, potassium carbonate and the like) and the like.

The acid to be used in the above-mentioned step for obtaining the crystalline or crystallized acid addition salt of Losartan is capable of forming a crystalline or crystallized acid addition salt together with Losartan, as mentioned above. For example, hydrochloric acid, hydrobromic acid and p-toluenesulfonic acid can be used. It is preferably p-toluenesulfonic acid because it can be purified to a particularly high level. These acids are used in an amount of generally 1–5 moles, preferably 1–2 moles per 1 mole of Losartan.

The method for forming the crystalline or crystallized acid addition salt in the above-mentioned step is not particularly limited. It is preferably a method comprising forming the salt in an organic solvent, wherein, for example, an acid or an organic solvent containing an acid is added to an organic solvent containing Losartan; Losartan or an organic solvent containing Losartan is added to an acid or an organic solvent containing an acid; or other method is employed. As used herein, by "forming a crystalline or crystallized acid addition salt in an organic solvent" is meant forming a crystalline or crystallized acid addition salt in a reaction solvent mainly containing an organic solvent. Therefore, this reaction solvent may contain a solvent such as water and the like, as long as it does not adversely influence the formation of the crystalline or crystallized acid addition salt.

The above-mentioned organic solvent is free of any particular limitation as long as it can dissolve Losartan. Preferably, an aromatic solvent such as MCB, toluene and the like; ethers such as THF and the like; esters such as ethyl acetate and the like; ketones such as methyl isobutyl ketone and the like; lower alcohols having 1 to 4 carbon atoms such as methanol, ethanol, propanol, butanol and the like; and the like. These organic solvents may be used in combination of two or more kinds of solvents. More preferably, it is THF or a mixed solvent of MCB and THF (preferably containing MCB in a proportion of not more than. 50 wt %). The organic solvent can be used in a least possible amount necessary for the formation of a crystalline or crystallized acid addition salt. It is generally used in an amount of 5–50 ml, preferably 10–25 ml, per 1 g of Losartan.

Depending on the kind of the solvent present in the reaction system, moreover, the obtained crystalline or crystallized acid addition salt can be a solvate of the solvent. When the obtained solvate has a high purity, the step for obtaining a crystalline or crystallized acid addition salt is preferably performed in a solvent capable of forming the solvate. Of the crystalline or crystallized acid addition salts, a THF solvate having a particularly high purity can be formed from Losartan and p-toluenesulfonic acid. When p-toluenesulfonic acid is used as an acid, the step is preferably performed in a solvent containing THF.

The temperature employed in the above-mentioned method is not particularly limited, and is determined according to the combination of Losartan, acid and organic solvent, and the like. It is generally 0–80° C., preferably 10–60° C. In addition, the reaction time is not particularly limited, either, and is generally 1–50 hours, preferably 1–20 hours.

The crystalline or crystallized acid addition salt formed by the above-mentioned method can precipitate into a reaction mixture. Therefore, it can be separated from the reaction mixture by a general separation method, for example, filtration, centrifugation, decantation and the like. When the precipitation does not occur due to high solubility and the like, precipitation can be promoted by a conventional method such as cooling and the like.

The purification method of the present invention preferably includes a step for obtaining a crystallized acid addition salt, because a crystallized acid addition salt has a particularly high purity. Therefore, the above-mentioned conditions (e.g., acid, solvent, temperature and the like) are preferably set in such a manner that a desired crystallized acid addition salt is obtained.

The above-mentioned crystalline or crystallized acid addition salt can be further purified by a conventional method as necessary, such as recrystallization, chromatography and the like.

The above-mentioned crystalline or crystallized acid addition salt can be easily converted to free Losartan or a salt at the tetrazole moiety thereof according to a conventional method. For example, by adjusting the pH to about 3.5–3.6, free Losartan can be obtained. By adjusting the pH to not less than 12 with aqueous caustic potash solution in aqueous acetonitrile, a potassium salt of Losartan can be obtained.

Losartan or a salt at the tetrazole moiety thereof (particularly potassium salt) obtained according to the above-mentioned purification method of the present invention, can have a purity high enough as a pharmaceutical preparation even without a complicated purification step, because a crystalline or crystallized acid addition salt can be purified to have a high purity. According to the purification method of the present invention, the steps necessary for achieving such high purity are less in number, and highly pure Losartan and a salt at the tetrazole moiety thereof (particularly potassium salt) can be obtained at a higher yield than that conventionally achieved.

The present invention is explained in more detail in the following by referring to Examples and Comparative Examples. The present invention is not limited by the following Examples.

The LC purity was determined by separating a sample by high performance liquid chromatography (HPLC) under the following conditions, and calculating the area percentage thereof.
(HPLC conditions)
Column; SUMIPAX ODS A-212 6 mmφ×15 cm (Sumika Chemical Analysis Service, Ltd.)
Mobile phase; acetonitrile: 0.1% aqueous acetic acid= 60:40 Flow rate; 1.0 mL/min
Column temperature; 35° C. Detection; UV 254 nm

EXAMPLE 1

To a THF-MCB solution (THF : MCB=1:2(weight ratio); 654.1 g) containing crude Losartan (43.9 g; LC purity 92.6%) was added a 5% aqueous caustic potash solution (136.8 g), and a 20% aqueous caustic potash solution was added to adjust the pH to not less than 12.5. The organic layer was separated to give an aqueous potassium salt solution (278.4 g) of Losartan. Then, THF (245 g) and MCB (210 g) were added to the aqueous solution and 17.5% aqueous hydrochloric acid was added to adjust the pH to 3.5–3.6, which was followed by partitioning. Active carbon (2.1 g) was added to the obtained organic layer and the mixture was stirred for 30 min for decoloration. The active carbon was filtered off and washed with a mixed solution of THF (10 g) and MCB (5 g) to give a THF-MCB solution containing crude Losartan (570.6 g; Losartan content 42.6 g; LC purity 95.5%).

p-Toluenesulfonic acid monohydrate (21.0 g) was dissolved in THF (21.0 g) and the solution was added in a thin stream to the THF-MCB solution at room temperature over 1 hr. The mixture was stirred overnight. After filtration, the obtained product was washed with a mixed solution of THF (42.0 g) and MCB (21.0 g) and dried to give a p-toluenesulfonate-THF solvate of Losartan as crystals [49.5 g; LC purity 99.60%; yield 71.5% (relative to crude Losartan in the initial THF-MCB solution)].

mp 118–120° C. (foamed upon dissolution) Elemental analysis: $C_{33}H_{39}N_6O_5ClS$ (Mw 667.233) Calculated C: 59.40; H: 5.89; N: 12.60; Found C: 59.30; H: 5.70; N: 12.60; IR(KBr): 3369, 1229, 1174, 1031, 1010, 682, 568 cm$^{-1}$ 1H-NMR(DMSO-d$_6$, 400 MHz, δ ppm): 0.78(3H,t), 1.21 (2H,m), 1.42(2H,m), 1.74(4H,m,THF), 2.28(3H,s), 2.57 (2H,m), 3.59(4H,m,THF), 4.35(2H,s), 5.33(2H,s), 6.98–7.10(6H,m), 7.47–7.69(6H,m).

The obtained p-toluenesulfonate-THF solvate crystals (6.7 g) of Losartan was dissolved in 50% (V/V) aqueous acetonitrile (70 ml) and 20% caustic potash solution was added in a thin stream at 15–25° C. to adjust the pH to 3.5–3.6. The precipitated crystals were collected by filtration, washed with 20% aqueous acetonitrile (18 ml) and water (18 ml), and dried to give Losartan (3.9 g; LC purity 99.67%; yield 93.0%).

Recrystallization from THF gave Losartan having an LC purity of.99.92%.

EXAMPLE 2

In the same manner as in Example 1 except that 35% hydrochloric acid (23.0 g) was used instead of the solution of p-toluenesulfonic acid monohydrate dissolved in THF, Losartan hydrochloride crystals (44.7 g; LC purity 98.67%; yield 93.7%) were obtained.

mp 188–196° C. (decomposition) Elemental analysis: $C_{22}H_{24}N_6OCl_2$ (Mw 459.382) Calculated C: 57.52; H: 5.27; N: 18.29; Found C: 57.30; H: 5.30; N: 18.30; IR(KBr): 3309, 1495, 1473, 1067, 1026, 1015, 999, 846, 780, 756, 743 cm$^{-1}$.

EXAMPLE 3

In the same manner as in Example 1 except that 48% hydrobromic acid (20.0 g) was used instead of the solution of p-toluenesulfonic acid monohydrate dissolved in THF, Losartan hydrobromide crystals (41.1 g; LC purity 98.50%; yield 78.0%) were obtained.

mp 186–210° C. (decomposition) Elemental analysis: $C_{22}H_{24}N_6OBrCl$ (Mw 503.838) Calculated C: 52.45; H: 4.80; N: 16.68; Found C: 51.70; H: 4.90; N: 16.50; IR(KBr): 3340, 1498, 1474, 1064, 1026, 1014, 999, 823, 779, 756, 743 $cm^{-1}$.

COMPARATIVE EXAMPLE 1

To a THF-MCB solution (THF: MCB=1:2 (weight ratio); 654 g) containing crude Losartan (43.9 g; LC purity 92.6%) was added 5% aqueous caustic potash solution (136.8 g), and 20% aqueous caustic potash solution was added to adjust the pH to not less than 12.5. The organic layer was separated to give an aqueous potassium salt solution of Losartan. Then, THF (210 g) was added to the aqueous solution and 17.5% aqueous hydrochloric acid was added to adjust the pH to 3.5–3.6. Active carbon (2.1 g) was added to the obtained organic layer and the mixture was stirred for 30 min for decoloration. The active carbon was filtered off and washed with THF (20 g). Ethyl acetate (920 g) was added to a mixture of the filtrate and washing solution, and the solvent (960 g) was evaporated under reduced pressure. The residue was stirred at 20° C. for 1 hr to allow precipitation of crystals. The crystals were collected by filtration, washed with ethyl acetate (20 g) and dried to give Losartan (36.8 g; LC purity 97.94%; yield 84.0%).

COMPARATIVE EXAMPLE 2

To a THF-MCB solution (THF: MCB=1:2 (weight ratio); 654 g) containing crude Losartan (43.9 g; LC purity 92.6%) was added a 5% aqueous caustic potash solution (136.8 g) and a 20% aqueous caustic potash solution was added to adjust the pH to not less than 12.5. The organic layer was separated to give an aqueous potassium salt solution of Losartan. Then, THF (245 g) and MCB (210 g) were added to the aqueous solution, and 17.5% aqueous hydrochloric acid was added to adjust the pH to 3.5–3.6. Active carbon (2.1 g) was added to the obtained organic layer and the mixture was stirred for 30 min for decoloration. The active carbon was filtered off and washed with a mixture of THF (10 g) and MCB (5 g). The solvent (200 g) was evaporated from a mixture of the filtrate and washing solution under reduced pressure. The residue was stirred at 20° C. for 1 hr to allow precipitation of crystals. The crystals were collected by filtration, washed with MCB (20 g) and dried to give Losartan (38.1 g; LC purity 95.74%; yield 86.8%).

The crystalline or crystallized acid addition salt of Losartan of the present invention is useful for obtaining highly pure Losartan, because it can be purified to have a high purity. In addition, the purification method of Losartan of the present invention affords highly pure Losartan with ease.

This application is based on applications Nos. 346829/1999 and 282853/2000 filed in Japan, the contents of which are incorporated hereinto by reference.

What is claimed is:

1. A crystalline or crystallized acid addition salt of 2-n-butyl-4-chloro-1-[[2'-(1H-tetrazol-5-yl) [1,1'-biphenyl]-4-yl]methyl]-1H-imidazole-5-methanol the formula (I)

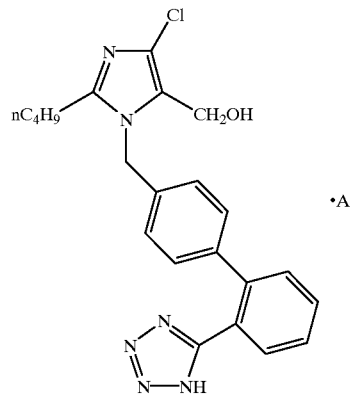

(I)

wherein A is p-toluenesulfonic acid·THF, hydrochloric acid, or hydrobromic acid, and wherein the acid addition salt has a liquid chromatography purity of at least 99.60% when A is p-toluenesulfonic acid·THF, wherein the acid addition salt has a liquid chromatography purity of at least 98.67% purity when A is hydrochloric acid, and wherein the acid addition salt has a liquid chromatography purity of at least 98.50% when A is hydrobromic acid.

2. The crystalline or crystallized acid addition salt of claim 1, wherein A is p-toluenesulfonic acid·THF.

3. A method for purifying 2-n-butyl-4-chloro-1-[[2'-(1H-tetrazol-5-yl)[1,1'-biphenyl]-4-yl]methyl]-1H-imidazole-5-methanol, which comprises a step of obtaining a crystalline or crystallized acid addition salt of the formula (I)

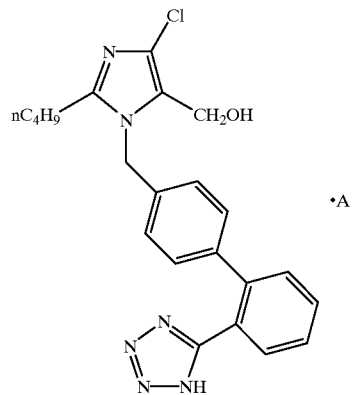

(I)

wherein A is p-toluenesulfonic acid·THF, hydrochloric acid, or hydrobromic acid, formed from 2-n-butyl-4-chloro-[[2'-(1H-tetrazol-5-yl) [1,1'-biphenyl]-4-yl]methyl]- 1 H-imidazole-5-methanol and either p-toluenesulfonic acid, hydrochloric acid, or hydrobromic acid, respectively, wherein the acid addition salt has a liquid chromatography purity of at least 99.60% when A is p-toluenesulfonic acid·THF, wherein the acid addition salt has a liquid chromatography purity of at least 98.67% purity when A is hydrochloric acid, and wherein the acid addition salt has a liquid chromatography purity of at least 98.50% when A is hydrobromic acid.

4. The method of claim 3, wherein the acid A is p-toluenesulfonic acid·THF.

5. The method of claim 3, wherein the salt is formed in an organic solvent.

6. The method of claim 5, wherein the solvent is tetrahydrofuran.

* * * * *

UNITED STATES PATENT AND TRADEMARK OFFICE
CERTIFICATE OF CORRECTION

PATENT NO. : 6,350,880 B1
DATED : February 26, 2002
INVENTOR(S) : Katsura et al.

It is certified that error appears in the above-identified patent and that said Letters Patent is hereby corrected as shown below:

Title page,
Item [30], Foreign Application Priority Data:

"Sep. 19, 2000     (JP) ……………………. 12-282853" should read as -- Sep. 19, 2000     (JP)…………………….2000-282853 --.

Item [56], References Cited, FOREIGN PATENT DOCUMENTS:

"WO    WO 98/18787    5/1998"
should read as -- WO    98/18787    5/1998 --.

Column 7,
Line 67, insert -- of -- before "the formula (I)".

Signed and Sealed this

Tenth Day of September, 2002

Attest:

Attesting Officer

JAMES E. ROGAN
Director of the United States Patent and Trademark Office